United States Patent [19]

Miller et al.

[11] Patent Number: 4,832,575
[45] Date of Patent: May 23, 1989

[54] AUTOMATIC TEST SYSTEM FOR CHECK VALVE CLOSURE IN PUMP FOR LIQUID CHROMATOGRAPHY SYSTEM

[75] Inventors: Les A. Miller, San Jose; Shahin Tabanfar, Santa Clara; Chih-Hua Chung, Fremont, all of Calif.

[73] Assignee: Spectra Physics, San Jose, Calif.

[21] Appl. No.: 142,572

[22] Filed: Jan. 11, 1988

[51] Int. Cl.[4] .......................... F04B 49/06; F04B 49/10
[52] U.S. Cl. .......................................... 417/18; 417/20; 417/22; 417/53; 210/198.2
[58] Field of Search ..................... 417/53, 18, 20, 22, 417/63; 210/198.2

[56] References Cited

U.S. PATENT DOCUMENTS

| | | | |
|---|---|---|---|
| 3,779,457 | 12/1973 | Cornyn, Jr. et al. | 417/63 |
| 4,128,476 | 12/1978 | Rock. | |
| 4,137,011 | 1/1979 | Rock. | |
| 4,255,088 | 3/1981 | Newton et al. | 417/1 |
| 4,359,312 | 11/1982 | Funke et al. | 417/539 |
| 4,420,393 | 12/1983 | Smith | 210/198.2 |
| 4,552,513 | 11/1985 | Miller et al. | 417/265 |
| 4,600,365 | 7/1986 | Riggenmann | 417/265 |
| 4,705,459 | 11/1987 | Buisine | 417/53 |

OTHER PUBLICATIONS

Spectra-Physics SP8700 Solvent Delivery System, 12 pages, published for Spectra-Physics.

*Primary Examiner*—William L. Freeh
*Attorney, Agent, or Firm*—Ron Fish

[57] ABSTRACT

There is disclosed herein a pump check valve test system embodied in a pump control system which control pump speed based upon actual pressure and upon actual pump speed and desired flow rate. The check valve test system disables the portion of the control system which controls pump speed based upon desired flow rate during the test. The test is comprised of timing the time it takes the pump to rotate through the portion of each cycle wherein the check valve is supposed to close and comparing this time to a known value.

18 Claims, 3 Drawing Sheets

AUTOMATIC TEST SYSTEM FOR CHECK VALVE CLOSURE IN PUMP FOR LIQUID CHROMATOGRAPHY SYSTEM

BACKGROUND OF THE INVENTION

The invention pertains to the field of pumps for liquid chromatography systems, and, more specifically, to the field of systems to insure proper check valve closure for same.

In the prior art, check valve closure for injection pumps for liquid chromatography systems was checked by timing the time it takes the pump to move through the segment of a revolution where the valve was closing. Because such systems have control loops that control the motor speed in response to both pressure on the column input and desired flow rate with two separate control loops, each responsive to one of these criteria, such systems were not reliable. The reason for this was that the time taken by the pump to move through the segment of the revolution where the check valve was supposed to be closing varied by the action of the control loops in changing the motor speed. A more reliable indication of failure of the check valve was necessary.

SUMMARY OF THE INVENTION

According to the teachings of the invention, there is taught an apparatus and method for obtaining a reliable check valve closure indication. The apparatus of the invention functions in the environment where a pump for a liquid chraomatography (hereafter LC) system is controlled by two control loops, one responsive to actual pressure on the column input and providing an actual pressure feedback signal and the other responsive to the motor shaft speed and a user input regarding the desired constant flow rate through the column. The latter loop generates a target pressure which is compared to the actual pressure to generate an error signal which is used to control the motor speed and, thus, controls the flow rate. The apparatus of the invention measures the time it takes for the pump shaft to traverse the segment of each revolution when each check valve to be checked is supposed to close while holding the target pressure constant thereby eliminating the errors created by the control loops in the prior art.

DETAILED DESCRIPTION OF THE PREFERRED EMBODIMENT

Figure 1:
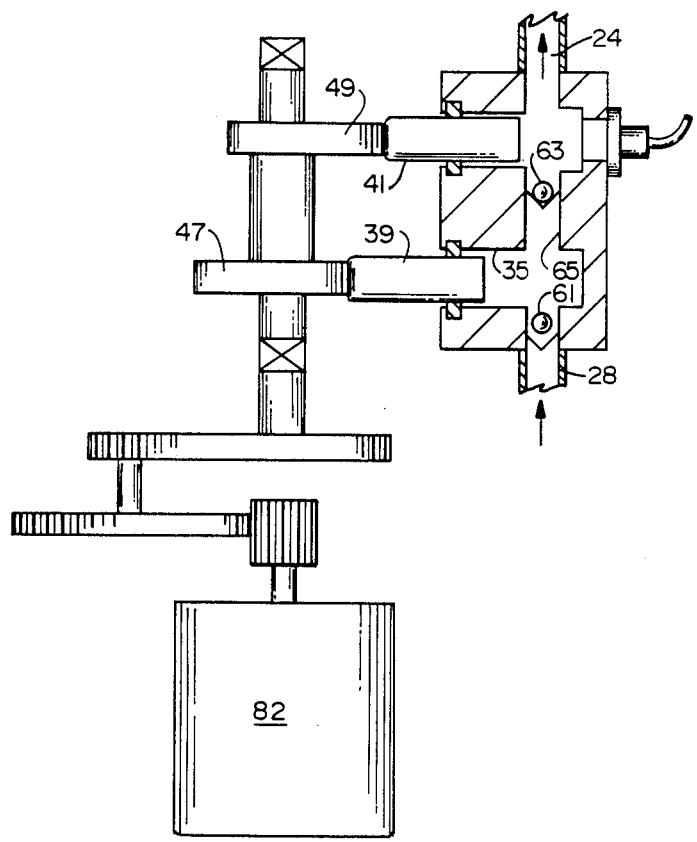
FIG. 1 is a diagram of a typical pump with check valves which can be monitored by the invention.

Referring to FIG. 1, there is shown a diagram of a typical pump used in LC systems to pump solvent into the column carrying the sample to be analyzed. The pump has a solvent input 28, a solvent output 24 connected to the LC column and two pistons 39 and 41. The pistons are driven by separate cams 47 and 49 so that their respective compression strokes are out of phase. An input check valve 61 allows only one way flow of solvent into the first cylinder 35 if it is working properly, and a second output check valve 63 allows only one way flow out of the pump outlet 24 under the influence of piston 41 during its compression stroke.

Figure 2:
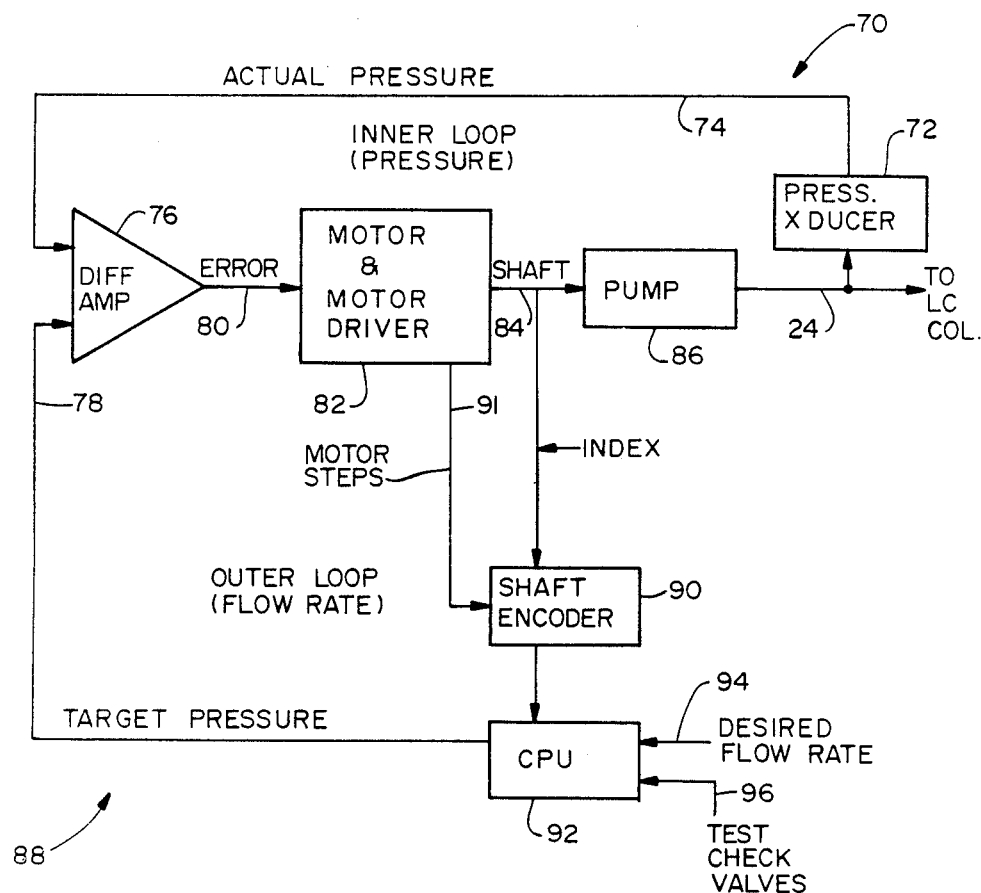
FIG. 2 is a diagram of the typical control loops used to control the pump of FIG. 1.

Referring to FIG. 2, there is shown a block diagram of the control system typically used with the pump of FIG. 1. The inner loop 70 senses the actual pressure on the outlet line 24 to the column via a pressure transducer 72 and uses the actual pressure signal from the transducer on line 74 as one input to a differential amplifier 76. The other input to this amplifier is the target pressure signal on line 78 from the outer loop. These two signals are compared to generate an error signal on line 80. The error signal is coupled to the motor driver and motor 82 and controls the motor speed. The motor drives a shaft 84 which drives the pump 86 such as shown in FIG. 1. The outer loop 88 senses the shaft speed via a shaft encoder or other device 90. The shaft encoder generates a signal used by a computer 92 to determine the pump speed and therefore to determine the flow rate of solvent in the output line 24. The computer also receives a desired flow rate signal on line 94 and uses this signal to compare to the actual flow rate as indicated by the signal from the shaft encoder to set a target pressure signal on line 78 to correct the actual flow rate to be the desired flow rate. The shaft encoder also provides data regarding the absolute shaft position relative to an index point. This data provides the computer with real time information as the actual position of each of the cams 47 and 49 and the status of the pistons 39 and 41 at each point in time. The motor 82 is actually a stepper motor and the motor driver puts out a series of positive and negative going pulses. The shaft encoder is coupled to count these pulses via line 91 and provide this information to the computer 92. Each motor step corresponds to a specific position of the shaft relative to an index position. By counting steps, the computer 92 knows the exact position of both cams at any time and can time the transition of the shaft between any pair of points in the rotation of the shaft.

In FIG. 1, it is apparent that the check valve 61 will open and the check valve 63 will close during the portion of the cycle when the piston 39 is in its input stroke. Conversely, check valve 61 will close and check valve 63 will open when piston is in its compression stroke. Likewise, check valve 63 will close when piston 41 is in its output stroke.

The satisfactory closing of the check valves can be determined by timing the time it takes the motor 82 to turn the cams through the portions of each revolution wherein each check valve is supposed to close. The reason this is true is that if the check valves are leaking, the pressure on the output line 24 will drop and the inner loop 70 will cause the motor to speed up. This speeding up will result in a shorter time through the given portion of the revolution which indicates the check valve being tested is leaking. But if the outer loop 88 is not disabled during this test, the target pressure may also change which also changes the motor speed for reasons which may not be related to check valve leakage. Thus, the invention disables the operation of the outer loop 88 during check valve test. This occurs when the computer 92 receives a test check valves input on line 96 from the user.

Figure 3:
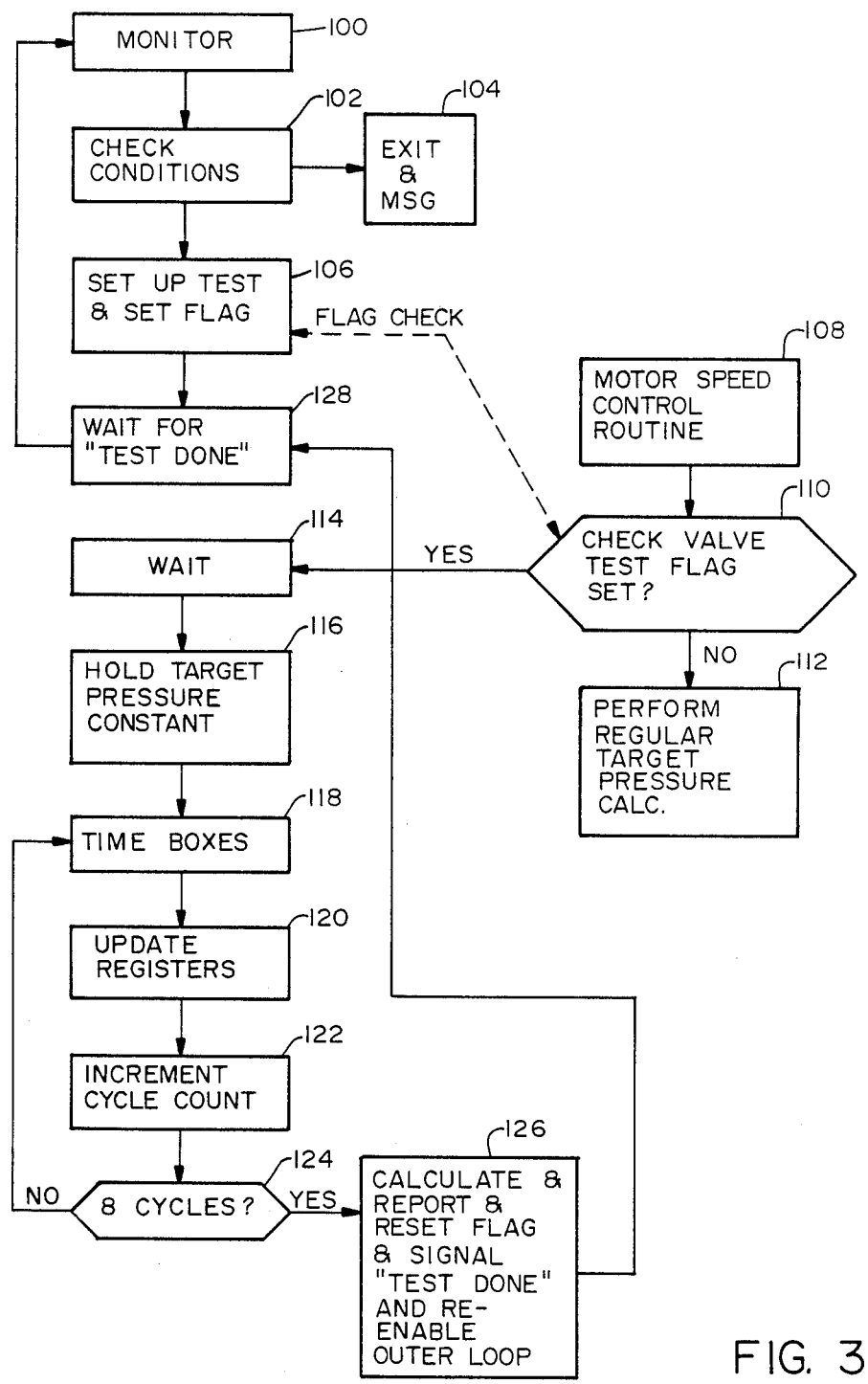
FIG. 3 is a flow chart of the program run in the computer in the invention to check the check valve closure.

Referring to FIG. 3, there is shown a flow chart of the program run by the computer 92 in performing the check valve test. The monitor step 100 represents the process of determining when the user desires the check valve test to be performed and supplies the test check valves signal. This may be performed periodically or randomly and may be automatically performed from time to time in some embodiments. The check conditions step 102 determines when a test is to be performed if conditions are proper to run a test. The check valve tests cannot be performed at high flow rates because of inaccuracies. Also, the test cannot be run when the pump is in a purge state. If conditions are not proper, step 104 is performed to exit and display a message to this effect. If conditions are proper, step 106 is performed. Step 106 sets up the test by writing values to the high and low time registers for each check valve. The test on each check valve involves timing the time it takes for the motor shaft to rotate from point A to point B where these two points define the portion of each revolution where the check valve under test is supposed to close. Points A and B are different for check valve 61 and for check valve 63 since they each close at different points in different portions of each revolution. The test for each check valve is run over 8 separate revolutions. The smallest time to traverse from point A to point B in any of the 8 revolutions is stored in a low time register, and the largest time to traverse from points A to B in any revolution is recorded in a high time register. There is a high time and low time register for each check valve. The set up step records a very high time for initial writing in the low time register for each check valve, and records a very low time for writing in the high time register prior to the first revolution. On each revolution, the time to traverse from points A to B is compared to the low time and high time "records" and if either record is exceeded, the appropriate register is updated with the new "record". This is done because the check valves do not fail reproducibly so an average over 8 revolutions is a more reliable indication. Finally, the set up step 106 sets a flag indicating the test is to be started when the motor shaft next reaches an appropriate position. This flag is monitored by the motor speed control routine which is run by the computer in generating the target pressure signal.

The motor speed control routine is symbolized by block 108. This routine includes a flag check, symbolized by step 110 which occurs just prior to each new calculation of a target pressure. If the flag is not set, step 112 is performed symbolizing the steps of normal outer loop operation in calculating and generating the new target pressure signal. If the flag is set, step 114 is performed to wait until the motor shaft is in the right position to begin the test. Then step 116 is performed to disable the operation of the outer control loop by holding the target pressure constant. This means that the only loop operating is the inner loop responding to actual pressure on the outlet. This eliminates errors that would result from changing of the target pressure during the test by the outer loop. The next step is 118 symbolizing the process of timing the time it takes for the motor shaft to rotate through the predetermined portion of each cycle where the input check valve is supposed to close and to rotate through the predetermined portion of each cycle where the input check valve is supposed to close. The elapsed time to traverse each "box", i.e., the predetermined portions of each cycle, is measured in step 118. Step 120 represents the process of updating the low and high registers for each check valve if a new low or high "record" is set. Step 122 increments the cycle count to keep track of the 8 cycles of testing.

Step 124 determines if the predetermined number of cycles of tests have been performed. If so, step 126 calculates the average time between the high and low records and reports the result. After this is done, the test flag is reset and a "test done" signal is sent to step 128 which then returns control to step 100. If step 124 indicates the test is not done, control is returned to step 118 to time the next cycle. Step 126 represents the process of subtracting the minimum time from the maximum time for each valve and dividing by the maximum time. The result is then compared to a known value to determine if the valve is good. Control is then returned to the pump speed control program of the outer loop to re-enable it. The Appendix A is the software which implements the flowchart of FIG. 3. The software listed in Appendix A will not be printed with the specification of this patent.

Although the invention has been described in terms of the preferred and various alternative embodiments disclosed herein, those skilled in the art will appreciate other alternative embodiments which do not depart from the true spirit and scope of the invention. All such embodiments are intended to be included within the scope of the claims appended hereto.

What is claimed is:

1. An apparatus for checking the integrity of a check valve in a pump comprising:
   means for controlling said pump using an error signal generated by comparing a signal based upon the actual pressure at the output of the pump to a flow rate control signal controlling the flow rate based upon actual pump speed and an input setting a desired flow rate;
   means for holding said flow rate control signal constant during said test and for timing the time it takes for said pump shaft to rotate through a predetermined portion of one revolution during which said check valve is supposed to close.

2. The apparatus of claim 1 further comprising means for causing said means for holding to time the appropriate portion of each revolution for a predetermined number of revolutions.

3. The apparatus of claim 2 further comprising means for providing programmability for the performance of said integrity test for said check valve such that said test may be performed either periodically or randomly.

4. The apparatus of claim 3 wherein said means for determining determines the flow rate and compares it to a constant to ensure that the flow rate is not too high to perform said integrity test.

5. The apparatus of claim 4 further comprising memory means for storing a high time and a low time for said check valve.

6. The apparatus of claim 2 further comprising means for determining if conditions are proper for a test prior to starting to time revolution times.

7. The apparatus of claim 6 further comprising means for displaying a message regarding test status when conditions are not proper for performing said integrity test and said integrity test has been requested.

8. The apparatus of claim 7 wherein said means for holding times the revolution time over the portion of each revolution when said check valve is supposed to close.

9. An apparatus for testing the quality of check valve closure in a pump for a liquid chromatography system using a control system which controls the shaft speed of said pump by generation of a target pressure control signal to control the flow rate so as to obtain a selected flow rate, comprising:

means for checking conditions of operation of said pump to insure that conditions are proper for performing said test;

means for setting a test flag;

means for controlling the pump speed by varying said target pressure control signal in such a manner to maintain said selected flow rate;

means in said means for controlling for periodically checking and said test flag to determine if said test flag is set;

means for waiting until said shaft is in the correct position to begin said test;

means for holding said target pressure constant;

means for timing the rotation of said pump shaft through a predetermined sector;

means for recording the time of rotation through said sector;

means for repeating the timing and recording steps a selected number of times; and means for examining said recorded times to determine the reliability of check valve closure.

10. The apparatus of claim 9 wherein said means for examining comprises means for subtracting the minimum time for closure from the maximum time for closure of said valve and for dividing the difference by said maximum time of closure.

11. The apparatus of claim 10 wherein said means for checking conditions comprises means for checking whether the flow rate is less than a predetermined flow rate and for preventing the setting of said test flag if said flow rate is above the predetermined flow rate.

12. The apparatus of claim 9 wherein said means for waiting comprises means for checking shaft position of said pump to determine when the shaft has reached a position at the start of a sector where said check valve is supposed to start closing.

13. The apparatus of claim 12 wherein said means for checking conditions further comprises means for determining if the pump is in a purge state and for preventing the setting of said test flag if said pump is in a purge state.

14. A method of testing the quality of check valve closure in a pump for a liquid chromatography system utilizing a control system which controls flow rate of said pump by controlling the shaft speed of said pump through the generation of a target pressure control signal, comprising:

determining if conditions are right for testing the quality of check valve closure;

holding said target pressure control signal constant during said test;

timing the time it takes said pump shaft to rotate through a predetermined sector of rotation for a plurality of rotations; and calculating the ratio equal to the maximum difference in times of rotation through said sector divided by the maximum time of rotation through said sector.

15. The method of claim 14 wherein said timing step includes the step of recording each time of rotation through said sector for each of a plurality of revolutions in a memory.

16. The method of claim 14 wherein said step of timing comprises the step of timing the time of rotation through that sector of a revolution of a pump shaft wherein said check valve is supposed to close.

17. The method of claim 16 wherein said step of determining conditions comprises the step of determining if the flow rate is less than a predetermined amount prior to performing said test.

18. A method of testing the integrity of check valve closure in a pump for a liquid chromatography system using a control system which controls flow rate in the system by generating a target pressure control signal which controls the shaft speed of said pump, comprising:

determining if conditions are right for running said test and setting a test flag when conditions are right;

controlling the flow rate in said system to be a selected flow rate by varying said target pressure control signal;

checking said test flag to determine if it is set when said test is to be performed;

holding said target pressure signal constant during said test;

recording the time of rotation of said pump shaft through a predetermined sector of rotation of said pump shaft during which said check valve is supposed to close during each of a plurality of revolutions; and calculating the ratio equal to the difference between the maximum time of rotation through said sector for all revolutions minus the minimum time of rotation through said sector for all revolutions, said difference divided by said maximum time.

* * * * *

UNITED STATES PATENT AND TRADEMARK OFFICE
CERTIFICATE OF CORRECTION

PATENT NO. : 4,832,575

DATED : May 23, 1989

INVENTOR(S) : Les A. Miller, Shahin Tabanfar, Chih-Hua Chung

It is certified that error appears in the above-identified patent and that said Letters Patent is hereby corrected as shown below:

ON THE TITLE PAGE, Item [73]

The Assignee should be --Spectra-Physics, Inc., San Jose, Calif.--

Signed and Sealed this

Twenty-ninth Day of December, 1992

*Attest:*

DOUGLAS B. COMER

*Attesting Officer*  *Acting Commissioner of Patents and Trademarks*